United States Patent [19]

Wertheimer et al.

[11] 4,037,964
[45] July 26, 1977

[54] METHOD AND APPARATUS FOR MEASURING THE SUM OF THE RADII OF PARTICLES IN A COLLECTION

[75] Inventors: Alan Lee Wertheimer, North Wales; Frederick Lee Williams, Lansdale, both of Pa.

[73] Assignee: Leeds & Northrup Company, North Wales, Pa.

[21] Appl. No.: 649,754

[22] Filed: Jan. 15, 1976

[51] Int. Cl.² ............................................. G01N 15/02
[52] U.S. Cl. ................................ 356/102; 350/162 SF
[58] Field of Search ................... 356/102; 350/162 SF

[56] References Cited

U.S. PATENT DOCUMENTS

| | | | |
|---|---|---|---|
| 3,809,478 | 5/1974 | Talbot | 356/102 X |
| 3,873,206 | 3/1975 | Wilcock | 356/102 X |

*Primary Examiner*—John K. Corbin
*Assistant Examiner*—Matthew W. Koren
*Attorney, Agent, or Firm*—William G. Miller, Jr.; Raymond F. MacKay

[57] ABSTRACT

There is disclosed a Fraunhofer plane spatial filter design for use in filtering the forward scattered light from a collection of particles to obtain an indication of the sum of the radii of the particles as a direct function of the total diffracted light flux passed by the filter.

3 Claims, 2 Drawing Figures

4,037,964

METHOD AND APPARATUS FOR MEASURING THE SUM OF THE RADII OF PARTICLES IN A COLLECTION

BACKGROUND OF THE INVENTION

This invention relates to the measurement of the sum of a linear dimension of particles in a collection of particles by the use of the forward scattered light produced when a light beam is directed at the particle collection. More specifically, this invention relates to a measurement of the sum of the radii of the particles when they are spherical. There is specifically set forth the shape of a mask which can be used in the Fraunhofer plane for filtering the forward scattered light from a collection of particles so that a measurement of the light flux transmitted by that filter is directly related to the sum of the radii of the particles in the collection. The particular design for the mask disclosed is useful in optical systems such as that shown in U.S. Pat. No. 3,873,206 entitled "Method for Determining a Specific Characteristic of Fluid Suspended Particles", issued to William Leslie Wilcock on Mar. 25, 1975. That particular patent discloses a filter mask shaped to provide a third power response, that is a measure of the total volume of the particles in the collection being examined. A substitution of the mask design set forth in this application in the system of the Wilcock patent would provide an output which is proportional to the sum of the radii of all of the particles in the collection.

SUMMARY OF THE INVENTION

In carrying out this invention there is provided means for performing the method for determining the magnitude of the sum of a linear dimension of the individual particles of a collection of particles which comprises steps including the directing of a light beam at the collection of particles. There is then detected the light diffracted from the beam by the particles for the production of an output signal in response to the diffracted light attributable to individual particles in a manner such that the response has a predetermined functional relationship to the linear dimensions of the individual particles which relationship makes the total output proportional to the magnitude of the sum of the linear dimensions. The linear dimensions characteristically are the radii of the particles when they are spherical and the function is a direct function.

DESCRIPTION OF THE PREFERRED EMBODIMENT

Figure 1:
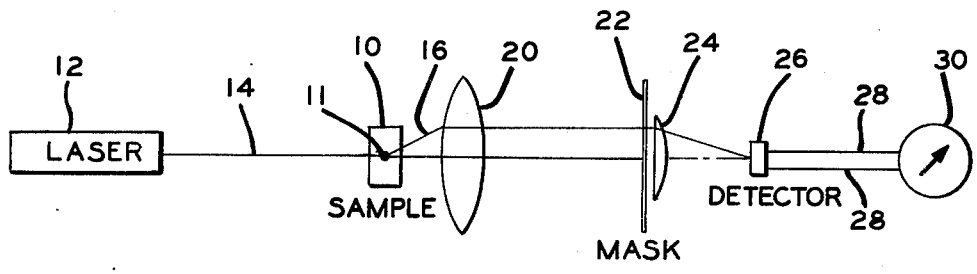
FIG. 1 is a diagram of the optical system which incorporates the novel mask design.

In FIG. 1 there is shown a diagram of the optical system which can be utilized with the novel mask design of this specification for the purpose of obtaining an indication of the sum of the linear dimension of the individual particles in a collection of particles. Specifically, when the particles are spherical in shape the indication is an indication of the sum of the radii of the individual particles of the collection. If the particles are not spherical the indication would be of an average linear dimension which would vary depending on particle shape. The collection of particles forming the sample in container 10 may, for example, be a sample of fluid suspended particles either contained within an enclosure or in a flowing stream. That sample is placed in a position such that a collimated light beam is directed at the particles as by the laser 12 which is shown in FIG. 1 directing a light beam 14 along the optical axis of the system. Particles such as particle 11 which are in the sample collection 10 and lie in the path of the light beam 14 cause a diffraction of the light beam at an angle as for example along path 16. The diffracted light is directed by a focusing element which consists of the collecting lens 20 through the mask 22 which lies in the Fraunhofer plane of lens 20. That portion of the diffracted light which passes through the mask 22 is focused by the lens 24 on detector 26. The detector 26 in turn produces on its output lines 28 a signal into indicator 30 indicative of the total light flux falling on the detector 26.

In FIG. 1 the mask 22 is shown in a side view. That mask may be rotated if desired for the purpose of averaging out any unsymmetrical characteristics in the sample collection.

Figure 2:
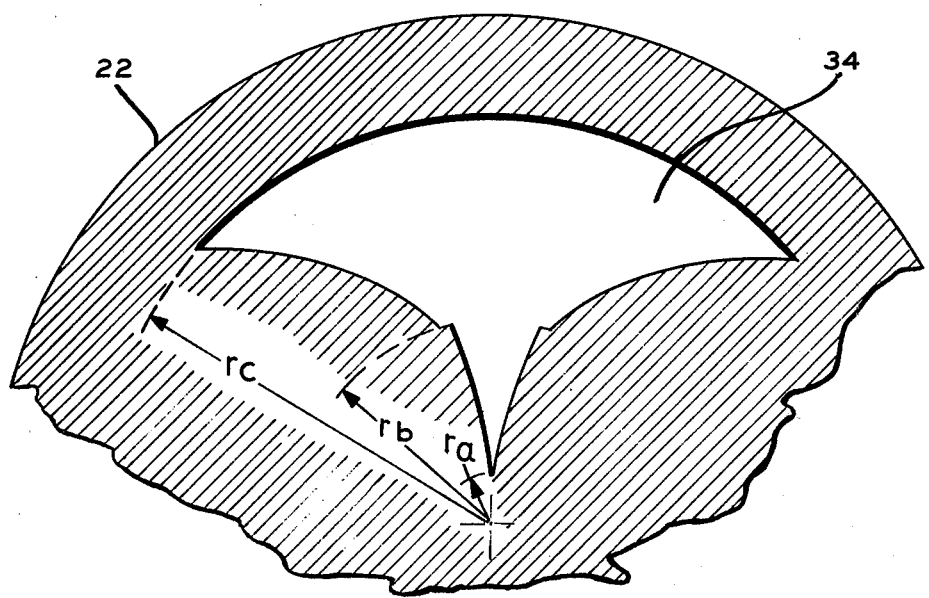
FIG. 2 is a drawing showing one form of the mask design.

In FIG. 2 there is shown one particular form which the mask can take (FIG. 2 being a front elevation of the mask 22). In general the opening 34 in the opaque mask 22 has a shape such that $\theta_i$ the angle over which the mask is open at any particular radius $r_i$ is determined by the following equation:

$$\theta_i = \theta_1 (r_i/r_1)^P$$

wherein $\theta_1$ is the angle over which the opening occurs at the inner radius of the zone of interest, $r_1$ is the inner radius of the zone of interest, and $r_2$ is the outer radius of that zone. The outer angle may be considered $\theta_2$ which is the opening existing at the radius $r_2$ while the exponent P has a value which is normally adjusted to give the desired response by the detector 26 of FIG. 1 with the mask design used. That exponent would be approximately equal to $(2 - N)$ following the teaching of the prior art in U.S. Pat. No. 3,809,478 issued to John Henry Talbot on May 7, 1974 where N is the exponent of the radius of the particles for the particular measurement being made. Thus, where the measurement is a measurement of the sum of the radii of the particles the exponential factor is theoretically 1 (N being equal to 1. It is, however, necessary to adjust the exponent to obtain a reasonably accurate measurement. This adjustment is required due to the finite boundaries of the opening in the mask.

It will be evident that the opening 34 of mask 22 may have any one of a number of different shapes which fulfill the requirements set forth above, however, a specific shape for the opening 34 using two zones is shown in FIG. 2. That shape is particularly applicable to an optical system as shown in FIG. 1 wherein the lens 20 has a focal length of 7.6 in. and the wavelength of the light beam 14 is 0.6328 $\mu$. The specific shape for opening 34 is described by the table below where the dimensions for the various parameters in each of two preselected zones is set forth with zone 1 being that area between the radii $r_a$ and $r_b$ and zone 2 being the area between the radii $r_b$ and $r_c$. The curvature of the boundaries of the mask in each of the zones is in accordance with the equation set forth above for $\theta_i$ where P is the particular filter function exponent set forth in the following table:

| Zone No. | $r_1$ Inner Radius (Inches) | $\theta_1$ Inner Angle (Degrees) | $r_2$ Outer Radius (Inches) | $(\theta_2)$ Outer Angle (Degrees) | P Exponent of Filter Fn. |
|---|---|---|---|---|---|
| 1 | .1650 | 3.424 | .6500 | 20.774 | 1.315 |
| 2 | .6500 | 28.630 | 1.3400 | 89.793 | 1.580 |

A mask designed as shown in FIG. 2 can produce a relatively constant response for a distribution of particles from approximately 2.5 μm. to well over 200 μm. Over that range responses within ±10% have been obtained.

The indication obtained on the meter 30 of FIG. 1 when using the mask of FIG. 2 gives as mentioned an indication of the total sum of the radius of the individual particles in the collection of particles which form the sample 10. That measurement can be utilized advantageously in statistical analysis of the distribution of the particles by their radius and when combined with others statistical parameters can be used for the determination, the mean of that distribution, its standard deviation, and also its skewness.

What is claimed is:

1. A spatial filter for the Fraunhofer plane of a lens of 7.6 in. focal length for filtering the forward scattered light diffracted from a collection of particles lying in the path of a light beam of 0.6328μ wavelength for passing an amount of light flux directly related to the sum of the radii of the particles lying in the path of said beam comprising, an opaque mask having a transparent area therein which is made up of two separate zones wherein the inner radius of each of the zones is $r_1$, the outer radius is $r_2$, the inner angle is $\theta_1$, and the outer angle is $\theta_2$ and the exponent of the filter function is P with the transparent opening being described by the table:

| Zone No. | $r_1$ Inner Radius (Inches) | $\theta_1$ Inner Angle (Degrees) | $r_2$ Outer Radius (Inches) | $(\theta_2)$ Outer Angle (Degrees) | P Exponent of Filter Fn. |
|---|---|---|---|---|---|
| 1 | .1650 | 3.424 | .6500 | 20.774 | 1.315 |
| 2 | .6500 | 28.630 | 1.3400 | 89.793 | 1.580 | with the boundaries of the transparent area between the inner and outer radius in each of the zones being in accordance with the equation:

$$\theta_i = \theta_1 (r_i/r_1)^P.$$

2. Apparatus for measuring the sum of the radii of the individual particles of a collection of particles comprising:

means for directing a light beam at said collection of particles, a filter for filtering the light diffracted from said beam by the particles of said collection, said filter having a filter function which varies between approximately 1.3 and 1.6 as the distance from the axis of said beam increases so that the magnitude of the total light flux transmitted is proportional to said sum, and means for detecting the magnitude of the total light flux transmitted by said filter as a measure of said sum.

3. Apparatus as set forth in claim 2 in which the filter function is 1.315 in the zone nearest the center of the filter and is 1.58 in the zone extending from the nearest zone to the outer limit of the mask.

* * * * *